United States Patent
Imoto et al.

(10) Patent No.: US 10,209,502 B2
(45) Date of Patent: Feb. 19, 2019

(54) MICROSCOPE AND MICROSCOPY METHOD

(71) Applicant: OLYMPUS CORPORATION, Tokyo (JP)

(72) Inventors: Kentaro Imoto, Tokyo (JP); Shinichi Takimoto, Tokyo (JP); Shintaro Takahashi, Tokyo (JP); Atsushi Doi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 172 days.

(21) Appl. No.: 15/275,359

(22) Filed: Sep. 24, 2016

(65) Prior Publication Data
US 2017/0010453 A1    Jan. 12, 2017

Related U.S. Application Data

(63) Continuation of application No. PCT/JP2015/061905, filed on Apr. 17, 2015.

(30) Foreign Application Priority Data

Apr. 24, 2014  (JP) .................................. 2014-090482

(51) Int. Cl.
*G02B 21/00*  (2006.01)
*G01N 21/64*  (2006.01)

(52) U.S. Cl.
CPC ..... *G02B 21/0076* (2013.01); *G01N 21/6458* (2013.01); *G02B 21/006* (2013.01);
(Continued)

(58) Field of Classification Search
CPC ............ G02B 21/0076; G02B 21/0032; G02B 21/006; G02B 21/0068; G02B 21/008;
(Continued)

(56) References Cited

U.S. PATENT DOCUMENTS 5,296,703 A * 3/1994 Tsien ................. G02B 21/0076
250/235
5,367,527 A * 11/1994 Gruneisen ............. H01S 3/2383
372/18
(Continued)

FOREIGN PATENT DOCUMENTS

JP          10-97642 A      4/1998
JP       2005-274591 A    10/2005
(Continued)

OTHER PUBLICATIONS

Bingen et al., "Parallelized STED fluorescence nanoscopy", Optics Express, vol. 19, No. 24, Nov. 21, 2011, pp. 23716-2372.*

(Continued)

*Primary Examiner* — Frank G Font
(74) *Attorney, Agent, or Firm* — Scully, Scott, Murphy & Presser, P.C.

(57) ABSTRACT

Provided is a microscope provided with: a scanner that scans an excitation beam coming from a light source; an objective optical system that focuses the scanned excitation beam onto a sample and that collects fluorescence generated at individual scanning positions in the sample; a detector that detects the collected fluorescence; a light blocking member that is disposed between the detector and the system and that partially blocks the collected fluorescence; a switching portion that switches the positional relationship between the member and a light-focusing point of the excitation beam in the sample between an optically conjugate positional relationship, in which an in-focus fluorescence generated at the light-focusing point passes through the member, and a non-conjugate positional relationship, in which the in-focus fluorescence is blocked by the member; and a computing portion that computes a difference between fluorescence (Continued)

signals acquired by the detector in the two positional relationships.

11 Claims, 13 Drawing Sheets

(52) U.S. Cl.
CPC ....... *G02B 21/008* (2013.01); *G02B 21/0032* (2013.01); *G02B 21/0068* (2013.01); *G02B 21/0084* (2013.01); *G01N 2201/06113* (2013.01); *G01N 2201/1053* (2013.01); *G01N 2201/12* (2013.01)

(58) Field of Classification Search
CPC ........... G02B 21/0084; G01N 21/6458; G01N 2201/06113; G01N 2201/1053; G01N 2201/12
USPC .................................................. 359/385, 388
See application file for complete search history.

(56) References Cited

U.S. PATENT DOCUMENTS

| | | | | |
|---|---|---|---|---|
| 6,094,300 | A * | 7/2000 | Kashima | G02B 21/16 356/317 |
| 6,128,077 | A * | 10/2000 | Jovin | G01J 3/10 356/310 |
| 6,462,345 | B1 * | 10/2002 | Simon | G02B 21/0056 250/458.1 |
| 6,496,267 | B1 * | 12/2002 | Takaoka | G01N 21/6458 356/317 |
| 6,642,504 | B2 * | 11/2003 | Cathey, Jr. | G02B 21/004 250/201.3 |
| 6,867,919 | B2 * | 3/2005 | Seyfried | G02B 27/283 250/201.3 |
| 7,092,086 | B2 * | 8/2006 | Knebel | G01J 3/44 356/301 |
| 7,339,148 | B2 * | 3/2008 | Kawano | G02B 21/002 250/201.3 |
| 2001/0012151 | A1 * | 8/2001 | Knebel | G02B 21/0076 359/368 |
| 2006/0238745 | A1 | 2/2006 | Koo et al. | |
| 2007/0014001 | A1 | 1/2007 | Ujike et al. | |
| 2007/0023686 | A1 | 2/2007 | Wolleschensky et al. | |
| 2007/0025662 | A1 * | 2/2007 | Gugel | G02B 21/0032 385/39 |
| 2007/0159690 | A1 * | 7/2007 | Ulrich | G02B 21/0032 359/385 |
| 2007/0290145 | A1 * | 12/2007 | Viellerobe | A61B 5/0062 250/459.1 |
| 2009/0021746 | A1 * | 1/2009 | Toida | A61B 5/0066 356/484 |
| 2009/0128898 | A1 | 5/2009 | Wolleschensky et al. | |
| 2010/0128221 | A1 * | 5/2010 | Muller | G02B 21/0028 351/207 |
| 2011/0036996 | A1 * | 2/2011 | Wolleschensky | G01N 21/6458 250/459.1 |
| 2011/0109958 | A1 * | 5/2011 | Yokoi | G02B 21/0032 359/363 |
| 2012/0098949 | A1 * | 4/2012 | Knebel | G02B 21/002 348/79 |
| 2012/0113506 | A1 * | 5/2012 | Gmitro | G02B 21/0028 359/385 |
| 2013/0128346 | A1 | 5/2013 | Sangu | |

FOREIGN PATENT DOCUMENTS

| | | |
|---|---|---|
| JP | 2006-023387 A | 1/2006 |
| JP | 2006-317544 A | 11/2006 |
| JP | 2009-510498 A | 3/2009 |
| JP | 2010-532878 A | 10/2010 |
| JP | 2012-78802 A | 4/2012 |
| JP | 2012-208442 A | 10/2012 |
| JP | 2013-019908 A | 1/2013 |
| JP | 2013-130853 A | 7/2013 |
| JP | 2015-190992 A | 11/2015 |
| WO | WO 2011/023593 A1 | 3/2011 |
| WO | WO 2011/052248 A1 | 5/2011 |
| WO | WO 2014/110290 A1 | 7/2014 |

OTHER PUBLICATIONS

English translation of WO2015-163251 provided by Google, Inc. at https://patents.google.com/patent/JPWO2015163261A1/en on May 8, 2018.*

Bertalmio, M., et al., "Image Inpainting", Proceeding of the 27th annual conference on computer graphics and interactive techniques, pp. 417-424.

International Search Report dated Jul. 14, 2015 issued in PCT/JP2015/061905.

International Search Report dated Dec. 22, 2015 issued in PCT/JP2015/076086.

* cited by examiner

MICROSCOPE AND MICROSCOPY METHOD

CROSS-REFERENCE TO RELATED APPLICATIONS

This is a continuation of International Application PCT/JP2015/061905 which is hereby incorporated by reference herein in its entirety.

This application is based on Japanese Patent Application No. 2014-090482, the contents of which are incorporated herein by reference.

TECHNICAL FIELD

The present invention relates to a microscope and a microscopy method.

BACKGROUND ART

In the related art, there are known microscopes that, in order to prevent leakage of off-focus fluorescence into a confocal pinhole from making it difficult to observe a portion deep inside a sample, discriminate in-focus fluorescence and off-focus fluorescence by using a separation member having a plurality of pinholes and a plurality of light detectors (for example, see Patent Literature 1).

CITATION LIST

Patent Literature

{PTL 1} Japanese Unexamined Patent Application, Publication No. 2005-274591

SUMMARY OF INVENTION

Solution to Problem

An aspect of the present invention provides a microscope including: a scanner that scans an excitation beam coming from a light source; an objective optical system that focuses the excitation beam scanned by the scanner onto a sample, and that, on the other hand, collects fluorescence generated at individual scanning positions in the sample; a detector that detects the fluorescence collected by the objective optical system; a light blocking member that is disposed between the detector and the objective optical system and that partially blocks the fluorescence collected by the objective optical system; a switching portion that switches, in a temporal manner, the positional relationship between the light blocking member and a light-focusing point of the excitation beam in the sample between an optically conjugate positional relationship, in which in-focus fluorescence generated at the light-focusing point passes through the light blocking member, and a non-conjugate positional relationship, in which the in-focus fluorescence does not pass through the same light blocking member as the light blocking member that has allowed the in-focus fluorescence to pass therethrough; and a computing portion that computes a difference between fluorescence signals acquired by the detector in the two positional relationships switched by the switching portion.

In addition, another aspect of the present invention provides a microscopy method in which an excitation beam scanned by a scanner is focused on a sample by using an objective optical system, fluorescence generated at the individual scanning positions in the sample is collected by using the objective optical system, and the fluorescence that has passed through a light blocking member is detected by a detector, the microscopy method including: a first step of detecting the fluorescence by using the detector by setting a positional relationship between the light blocking member and a light-focusing point of the excitation beam in the sample in an optically conjugate positional relationship in which in-focus fluorescence generated at the light-focusing point passes through the light blocking member; a second step of detecting the fluorescence by using the detector by setting the positional relationship between the light blocking member and a light-focusing point of the excitation beam in the sample in an optically non-conjugate positional relationship in which the in-focus fluorescence does not pass through the same light blocking member as the light blocking member that has allowed the in-focus fluorescence to pass therethrough; and a third step of subtracting fluorescence signals detected by the detector in the second step from fluorescence signals detected by the detector in the first step.

DESCRIPTION OF EMBODIMENT

A microscope 1 according to an embodiment of the present invention will be described below with reference to the drawings.

Figure 1:
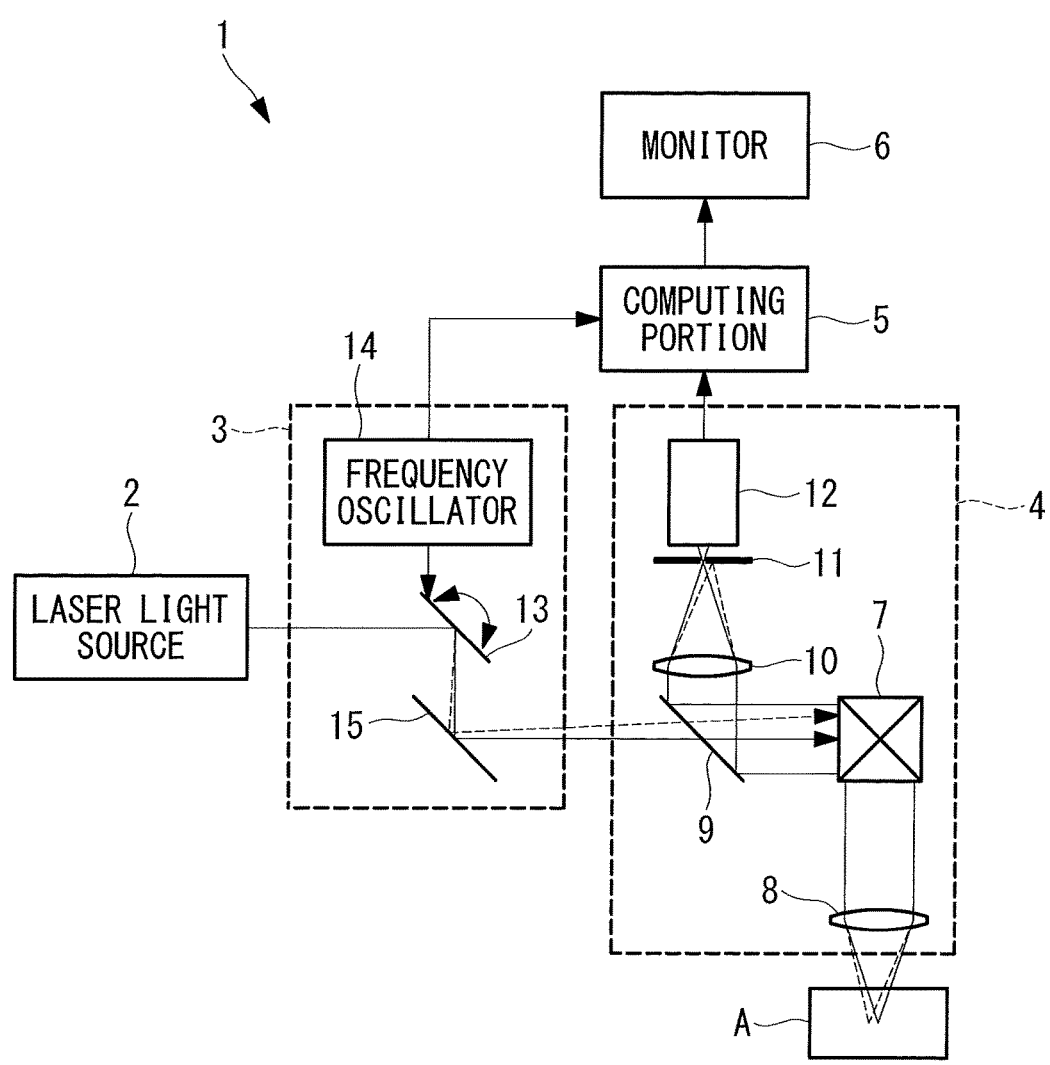
FIG. 1 is a diagram showing the overall configuration of a microscope according to an embodiment of the present invention.

As shown in FIG. 1, the microscope 1 according to this embodiment is provided with: a switching portion 3 that changes an excitation beam coming from a laser light source 2 into two alternately-emitted excitation beams; a microscope main unit 4 that radiates the two excitation beams changed by the switching portion 3 onto a specimen A and that detects fluorescence generated at the specimen A; a computing portion 5 that generates an image by means of computation using the fluorescence detected in the microscope main unit 4; and a monitor 6 that displays the image generated by the computing portion 5.

The microscope main unit 4 is provided with: a scanner 7 that two-dimensionally scans the excitation beams coming from the switching portion 3; an objective lens 8 that radiates the excitation beams scanned by the scanner 7 onto the specimen A and that collects the fluorescence coming from the specimen; a dichroic mirror 9 that splits off the fluorescence that is collected by the objective lens 8 and that returns via the scanner 7 from the optical path of the excitation beams; an imaging lens 10 that focuses the fluorescence that is split off by the dichroic mirror 9; a pinhole (light blocking member) 11 that is disposed at a position that is optically conjugate with the focal-point position of the objective lens 8; and a light detector 12 that detects the fluorescence that has passed through the pinhole 11. Note that, although the pinhole 11 is described as an example of the light blocking member, alternatively, it is permissible to employ an arbitrary light blocking member that allows in-focus fluorescence to pass therethrough when disposed at a position that is optically conjugate with the focal-point position of the objective lens 8 and that blocks in-focus fluorescence when disposed at a non-conjugate position. Other examples of the light blocking member include a micro-mirror device and a spatial light modulator.

The scanner 7 is, for example, a proximity galvanometer mirror formed by closely disposing two galvanometer mirrors that can be pivoted about non-parallel axes. The light detector 12 is, for example, a photomultiplier tube (PMT).

The laser light source 2 is a light source that continuously emits the excitation beam.

As shown in FIG. 1, the switching portion 3 is provided with: a movable mirror (deflection element) 13 whose pivoting angle is changed; and a frequency oscillator 14 that sets the frequency at which the movable mirror 13 is driven and is configured so as to alternately change the angles at which the excitation beam coming from the laser light source 2 enters the scanner 7 in synchronization with the frequency oscillated by the frequency oscillator 14. The reference sign 15 in the figure is a mirror. Note that, although a movable mirror is described as an example of the deflection element, it is also possible to use a device such as an acousto-optic deflector or an electro-optic deflector.

Figure 2:
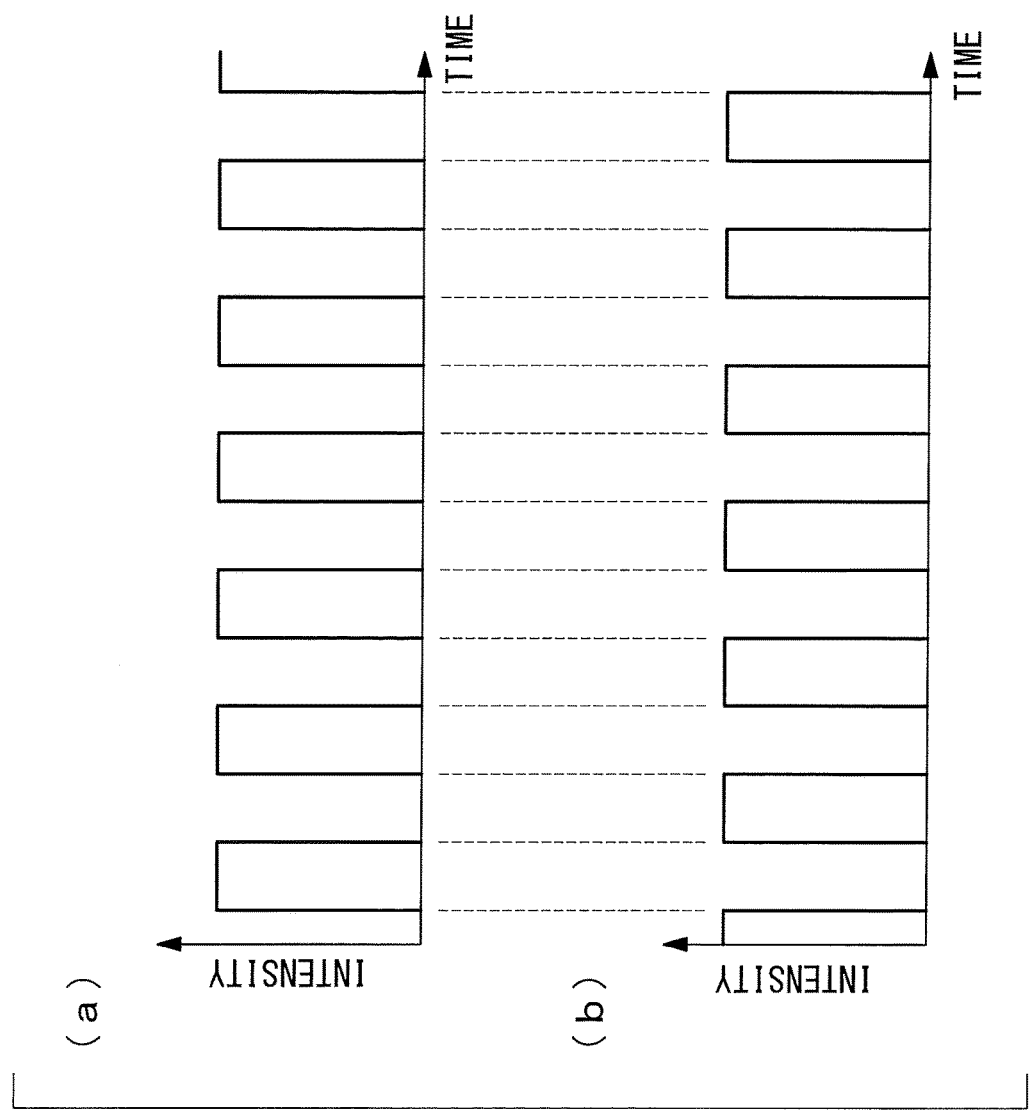
FIG. 2 is a diagram showing example patterns of two excitation beams that enter a microscope main unit from a light source of the microscope of FIG. 1.

By doing so, the two excitation beams having different incident angles are made to enter the microscope main unit 4 in an alternating manner. In other words, the two excitation beams that enter the microscope main unit 4 form rectangular waveforms having inverted timings, as shown in FIGS. 2(*a*) and (*b*). Note that, although beams that form rectangular waveforms having inverted timings are described here as examples of the two excitation beams, alternatively, it is permissible to employ excitation beams having arbitrary repeating shapes, such as sine waveforms or the like, and that have different phases.

One of the excitation beams, shown in FIG. 2(*a*), forms a focal point at a position that is optically conjugate with the pinhole 11 via the scanner 7 and the objective lens 8, and the other excitation beam, shown in FIG. 2(*b*), forms a focal point at a position that is optically non-conjugate with the pinhole 11 and via the scanner 7 and the objective lens 8. The frequency at which the incident angles are switched is set to a frequency at which the two excitation beams can flicker at least once at individual pixel positions.

Because the two excitation beams are alternately radiated onto the specimen A, the generated fluorescence are also alternately detected by the light detector 12 at different times.

The computing portion 5 calculates intensity differences of fluorescences generated by the two excitation beams and detected by the light detector 12 at the same pixel positions. The computing portion 5 is provided with, for example, a lock-in amplifier.

The lock-in amplifier is configured so as to calculate, by means of hardware, a difference between two fluorescence signals output from the light detector 12 in synchronization with the frequency generated by the frequency oscillator 14 to make the excitation beams flicker.

Thus, the computing portion 5 is configured to generate an image by storing the differences calculated for individual pixels and the positions scanned by the scanner 7 in association with each other.

The operation of the thus-configured microscope 1 according to this embodiment will be described below.

In order to perform fluoroscopy of the specimen A by using the microscope 1 according to this embodiment, the specimen A is placed on a stage (not shown) of the microscope main unit 4, and a continuous excitation beam is generated at the laser light source 2 in a state in which the focal-point position of the objective lens 8 is adjusted so as to be aligned with the specimen A.

Then, by changing the angle of the movable mirror 13 in the switching portion 3, two excitation beams are made to enter the microscope main unit 4 at different incident angles in accordance with the predetermined frequency oscillated by the frequency oscillator 14.

Because one of the excitation beams is consequently focused at a position in the specimen A that is conjugate with the pinhole 11, fluorescence generated in the vicinity of that focal-point position is collected by the objective lens 8, is separated by the dichroic mirror 9 in the process of returning via the scanner 7, is made pass through the pinhole 11 by being focused by the imaging lens 10, and is detected by the light detector 12 (first step).

In this case, when the specimen A is irradiated with the excitation beams, because the excitation beams excite fluorescent substances by passing through the specimen A also at an intermediate portion of a pathway leading to the focal-point position of the objective lens 8, fluorescences are generated not only at the focal-point position of the objective lens 8 but also at an intermediate portion of the pathway leading to the focal-point position. In particular, in the case in which the specimen A is formed of a scattering substance, fluorescence tends to be generated at portions other than the focal-point positions due to scattering of the excitation beams.

In addition, particularly when the NA of the excitation beams that are made to enter the specimen A in order to perform high-precision observation is increased, because the area of a region through which the excitation beams pass through before reaching the focal-point position is increased, fluorescence generated at portions other than the focal-point position is increased. In addition, because the area of the region through which the excitation beams pass is similarly increased when observing a deep portion, off-focus fluorescence is increased. Furthermore, it is necessary to increase the intensity of the excitation beams in order to compensate for the influence of scattering when observing a deep portion, and thus, the influence of off-focus fluorescence becomes particularly conspicuous.

Of the fluorescence generated at the specimen A, the fluorescence generated at the focal-point position of the objective lens 8 is detected by the light detector 12 as a signal beam because this fluorescence easily passes through the pinhole 11 disposed at the optically conjugate position; however, the fluorescence generated at the portions other than the focal-point position is scattered by the sample, and a portion thereof passes through the pinhole 11, thus being detected by the light detector as noise. Therefore, the fluorescence detected due to the irradiation of one of the excitation beams include the fluorescence generated at the focal-point position of the objective lens 8, which should be acquired as a signal, and the fluorescence generated at other portions (off-focus fluorescence), which should not be acquired as a signal.

In addition, the other excitation beam is focused at the position that is non-conjugate with the pinhole 11 in the specimen A and generates fluorescence by exciting fluorescent substances at the focal-point position of the objective lens 8 and at an intermediate portion of the pathway leading to the focal-point position.

In this case, the fluorescence generated at the non-conjugate focal-point position cannot pass through the pinhole 11, thus being blocked, whereas a portion of the fluorescence generated at the portions other than the focal-point position is scattered by the sample, passes through the same pinhole 11, and is detected by the light detector 12 in the same manner as in the previous step (second step).

Therefore, the fluorescence detected due to irradiation with the other excitation beam includes only the off-focus fluorescence generated at portions other than the focal-point position of the objective lens 8.

Then, the computing portion 5 computes the differences between the fluorescences detected due to irradiation with these two excitation beams (third step). By doing so, it is possible to acquire fluorescences from which the off-focus fluorescence, which has been generated at the portions other than the focal-point position of the objective lens 8 and should not be acquired as signals, have been removed.

Although areas in which the fluorescences are generated by irradiation with the two excitation beams do not exactly overlap, because most portions thereof overlap, and, by detecting the fluorescences by using the same pinhole, most of the off-focus fluorescence can be removed even if subtraction is performed without any manipulation. In particular, in the case in which high-precision observation is performed due to the increased NA of the excitation beams, because the proportion by which the areas in which the fluorescences are generated are overlapped is increased, it is possible to more effectively remove the off-focus fluorescence.

As has been described above, with the microscope 1 according to this embodiment, there is an advantage in that it is possible to detect the fluorescence generated at the focal-point position of the objective lens 8 at a high S/N ratio, and it is possible to acquire a low-noise, clear image. The microscope 1 according to this embodiment is highly effective particularly during high-definition observation in which the NA of the excitation beams is high, and in the case in which the specimen is a strong scattering substance, and thus, off-focus fluorescence tends to be generated.

In addition, in this embodiment, because differences between two fluorescences acquired at very small time intervals are computed for the individual pixels, there is an advantage in that it is possible to acquire a low-blur fluorescence image even when a fast-moving specimen is used.

Figure 3:
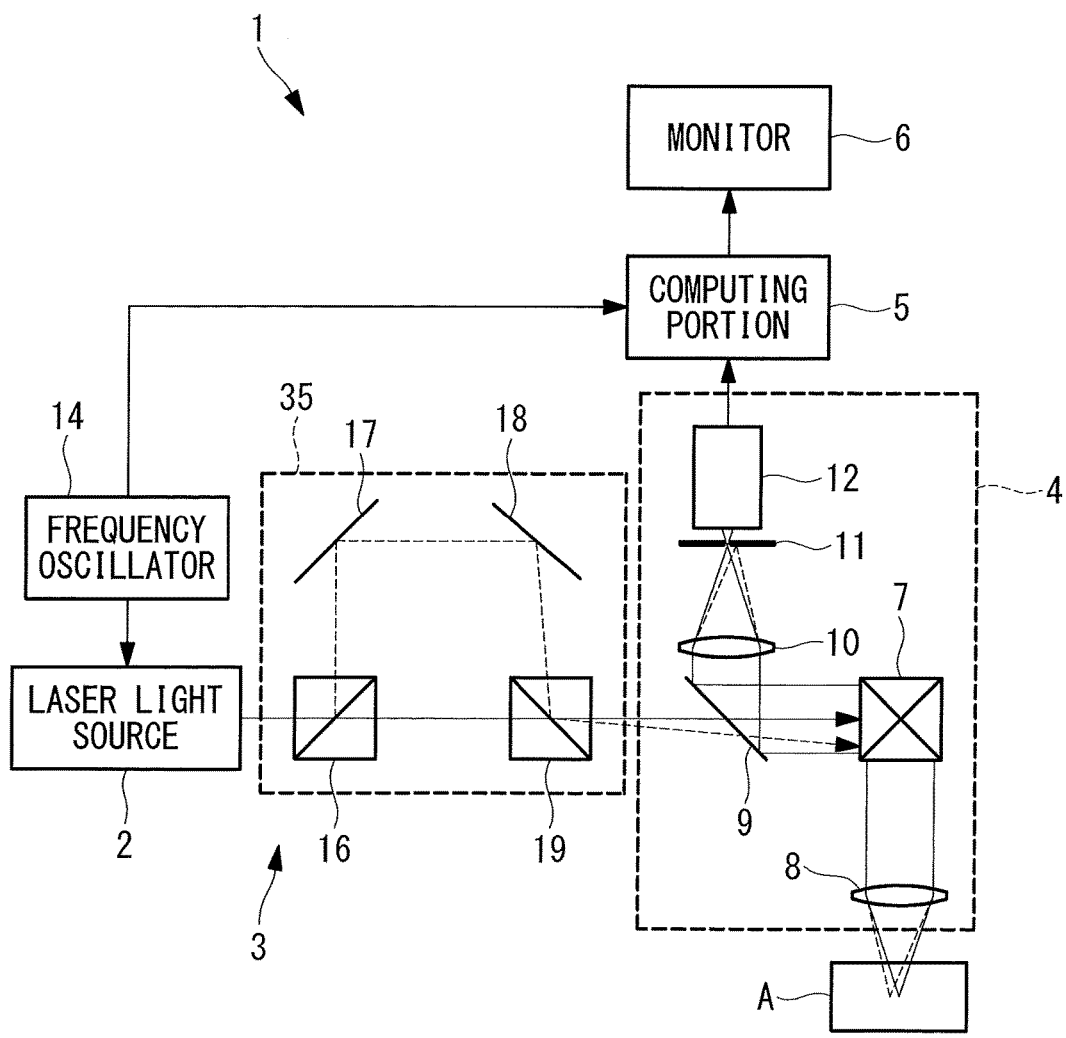
FIG. 3 is a diagram showing the overall configuration of a first modification of the microscope of FIG. 1.

Note that, in this embodiment, as the switching portion 3 that generates the two excitation beams that enter the scanner 7 at different angles and that flicker at inverted timings, a unit provided with the movable mirror 13 that makes the continuous excitation beam coming from the laser light source 2 enter the microscope main unit 4 at different angles has been described as an example; alternatively, however, as shown in FIG. 3, it is permissible to employ a spatial optical system (switching portion) 35 that splits the excitation beam coming from the laser light source 2 into two optical paths, thus generating two excitation beams that enter the scanner 7 at different angles and that have different phases.

In this case, laser light source 2 is connected to the frequency oscillator 14 and is configured so as to make the excitation beam oscillate in a repeating waveform, as shown in FIG. 2(*a*), at the predetermined frequency generated by the frequency oscillator 14. The frequency of the laser light source 2 is a frequency that is repeated for at least one cycle at the individual pixel positions.

As shown in FIG. 3, the spatial optical system 35 is provided with: a demultiplexer 16 (for example, a polarizing beam splitter) that splits the excitation beam coming from the laser light source 2 into two optical paths; mirrors 17 and 18 that make the optical-path lengths of the two optical paths split by the demultiplexer 16 different; and a multiplexing portion (for example, polarizing beam splitter) 19 that roughly combine the two excitation beams that have passed along the two optical paths split by the demultiplexer 16.

The mirrors 17 and 18 are set at positions and angles so that the excitation beams that have passed along the two optical paths split by the demultiplexer 16 flicker at inverted timings, as shown in FIGS. 2(*a*) and (*b*), and enter the scanner 7 at different angles.

By doing so, the excitation beam that has passed along a first optical path that passes through the demultiplexer 16 forms a focal point at a position that is optically conjugate with the pinhole 11 via the scanner 7 and the objective lens 8. On the other hand, the excitation beam that has passed along a second optical path, which is one of the two optical paths split by the demultiplexer 16 and that is made to bypass via the mirrors 17 and 18, forms a focal point at a position that is optically non-conjugate with the pinhole 11 via the scanner 7 and the objective lens 8.

Because the excitation beam that forms the focal point at the position that is optically conjugate with the pinhole 11 and the excitation beam that forms the focal point at the position that is non-conjugate with the pinhole 11 have inverted flickering timings, the generated fluorescences also have inverted phases and are detected by the light detector 12 at different times.

In order to perform fluoroscopy of the specimen A by using the thus-configured microscope 1, the excitation beam oscillated by the frequency oscillator 14 at the predetermined repeating frequency is emitted from the laser light source 2 in the state in which the focal-point position of the objective lens 8 is adjusted so as to be aligned with the specimen A.

When the excitation beam emitted from the laser light source 2 is made to enter the spatial optical system 35, the excitation beam is split into the two optical paths by the demultiplexer 16. The excitation beam that has passed through the demultiplexer 16 directly enters the multiplexing portion 19 via the first optical path, and enters the microscope main unit 4 after passing through the multiplexing portion 19.

One of the two excitation beams split at the demultiplexer 16 passes along the second optical path that is made to bypass by the mirrors 17 and 18, is subsequently multiplexed by the multiplexing portion 19, and enters the microscope main unit 4. At this time, by passing along an optical-path length that is longer than that of the first optical path, a time delay occurs in the excitation beam that has passed along the second optical path, and thus, the phase thereof is inverted from that that of the excitation beam that enters microscope main unit 4 after passing along the first optical path.

In addition, the excitation beam that has passed along the second optical path is multiplexed by the multiplexing portion 19, thus being returned to a substantially equivalent optical path as the excitation beam that has passed along the first optical path; however, the angle at which the excitation beam enters the scanner 7 is made different by setting the angle and the position of the mirror 18.

As a result, because the excitation beam that has passed along the first optical path is focused at the position in the specimen A that is conjugate with the pinhole 11, fluorescence generated in the vicinity of that focal-point position is collected by the objective lens 8, is separated by the dichroic mirror 9 in the process of returning via the scanner 7, is made to pass through the pin hole 11 by being focused by the imaging lens 10, and is detected by the light detector 12.

In this case also, as with the above-described embodiment, the fluorescence detected due to irradiation with the excitation beam that has passed along the first optical path includes the fluorescence generated at the focal-point position of the objective lens 8 and the off-focus fluorescence generated at other portions. In addition, the fluorescence detected due to irradiation with the excitation beam that has been made to pass along the second optical path includes only the off-focus fluorescence.

Then, the computing portion computes the differences between the fluorescences detected by irradiation with the excitation beams that have passed along these two optical paths, thus making it possible to detect the in-focus fluorescence from which the off-focus fluorescence has been removed.

With this embodiment, as compared with the case in which the two excitation beams are alternately switched by using the movable mirror 13, there is an advantage in that it is possible to very quickly switch between the excitation beams.

Figure 4:
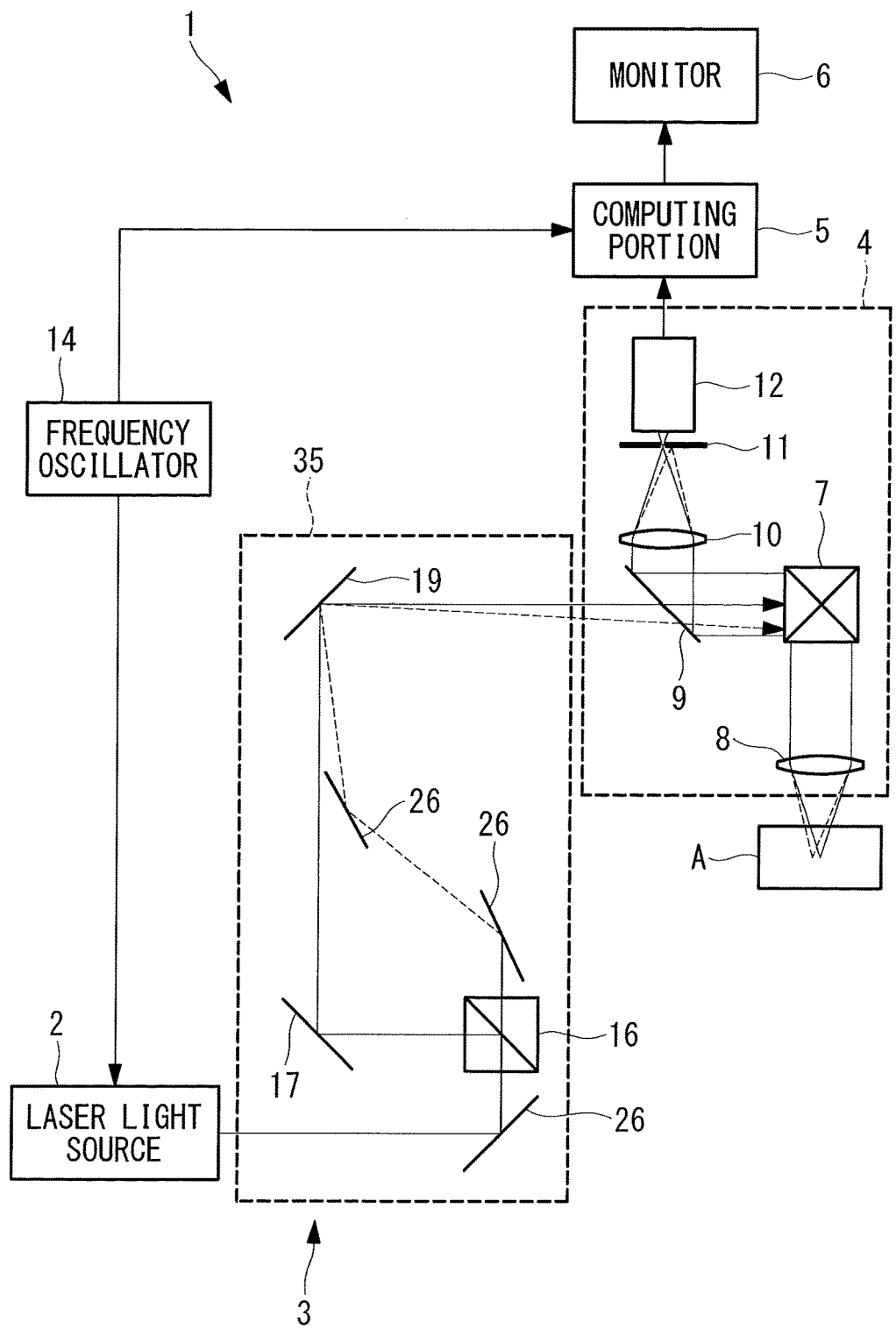
FIG. 4 is a diagram showing the overall configuration of an additional modification of the microscope of FIG. 3.

In this embodiment, although polarizing beam splitters have been described as examples of the demultiplexer 16 and the multiplexing portion 19, alternatively, non-polarizing beam splitters such as half mirrors may be employed. In addition, a mirror 19 shown in FIG. 4 may be employed as the multiplexing portion 19. The reference sign 26 in the figure indicates mirrors for forming the optical path.

Figure 5:
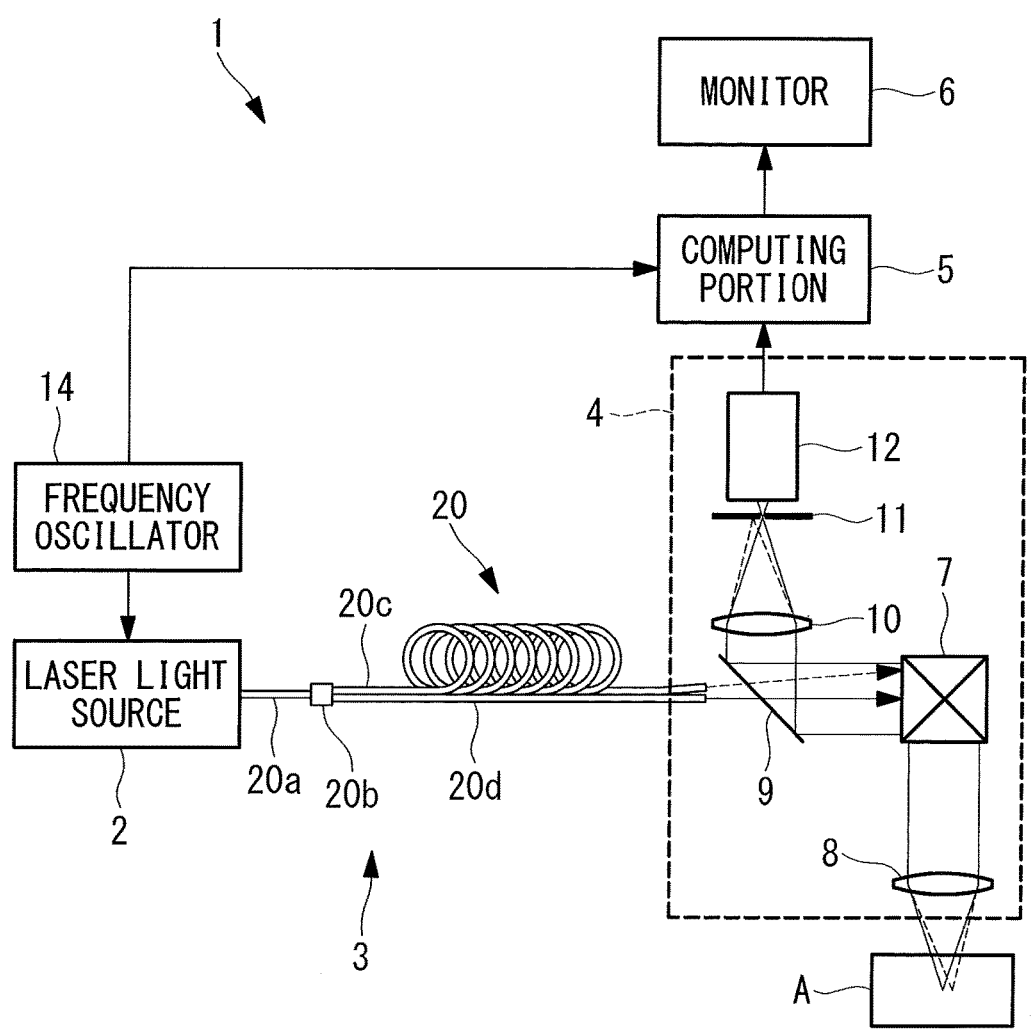
FIG. 5 is a diagram showing the overall configuration of a second modification of the microscope of FIG. 1.

In addition, in this embodiment, as shown in FIG. 5, optical fibers 20 may be employed instead of the spatial optical system 35 that generates the two excitation beams that enter the scanner 7 at different angles and that have inverted phases.

In the example shown in FIG. 5, a first optical fiber 20a into which a flickering excitation beam coming from the laser light source 2 is introduced is split into two second optical fibers 20c and 20d by a fiber beam splitter 20b; the lengths of the two second optical fibers 20c and 20d are made different; and the angles of the emitting ends thereof are also made different.

The lengths of the two second optical fibers 20c and 20d are different from each other to an extent sufficient to create an optical-path-length difference that is sufficient to completely invert the phases of the excitation beams that are emitted therefrom after being guided therethrough.

The second optical fiber 20c can be configured in a compact manner by being wound as shown in FIG. 5, thus making it possible to reduce the apparatus size.

Figure 6:
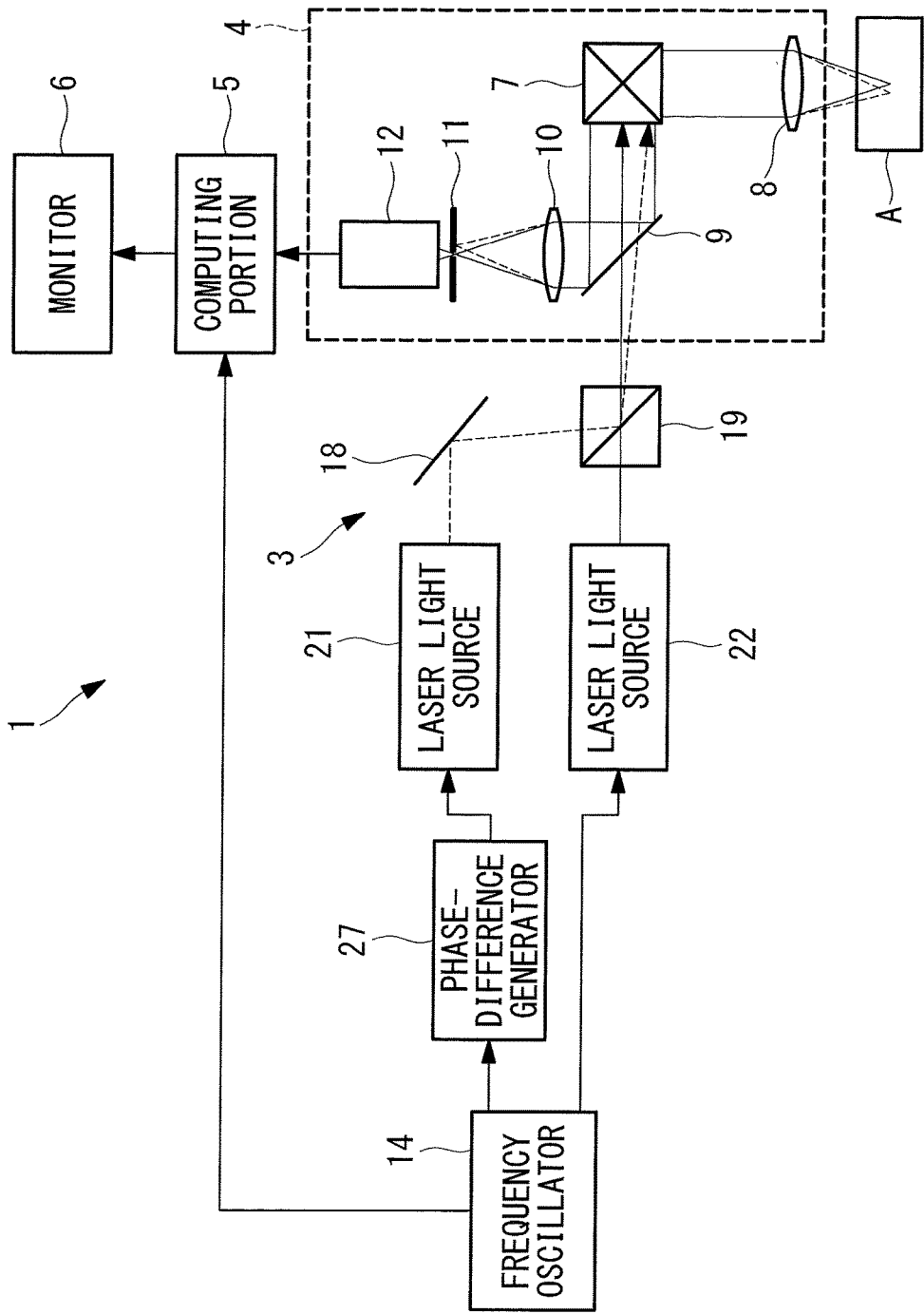
FIG. 6 is a diagram showing the overall configuration of a third modification of the microscope of FIG. 1.

In addition, instead of creating two excitation beams from the excitation beam coming from the single laser light source 2, as shown in FIG. 6, two laser light sources 21 and 22 that emit excitation beams that are made to oscillate in synchronization with each other but in inverted phase by means of a phase-difference generator 27 may be used, and the angles at which the excitation beams coming from the laser light sources 21 and 22 enter the scanner 7 may be made different by using the mirror 18 and the multiplexing portion 19. In this case, in the phase-difference generator 27, the switching portion 3 is formed of the mirror 18 and the multiplexing portion 19.

By doing so, it is possible to maintain the maximum laser output because the beam is not separated into two, and thus, it is possible to set the excitation-beam intensity high. In addition, it is possible to employ a compact configuration because the phase difference is imparted by synchronizing the laser beams.

Figure 7:
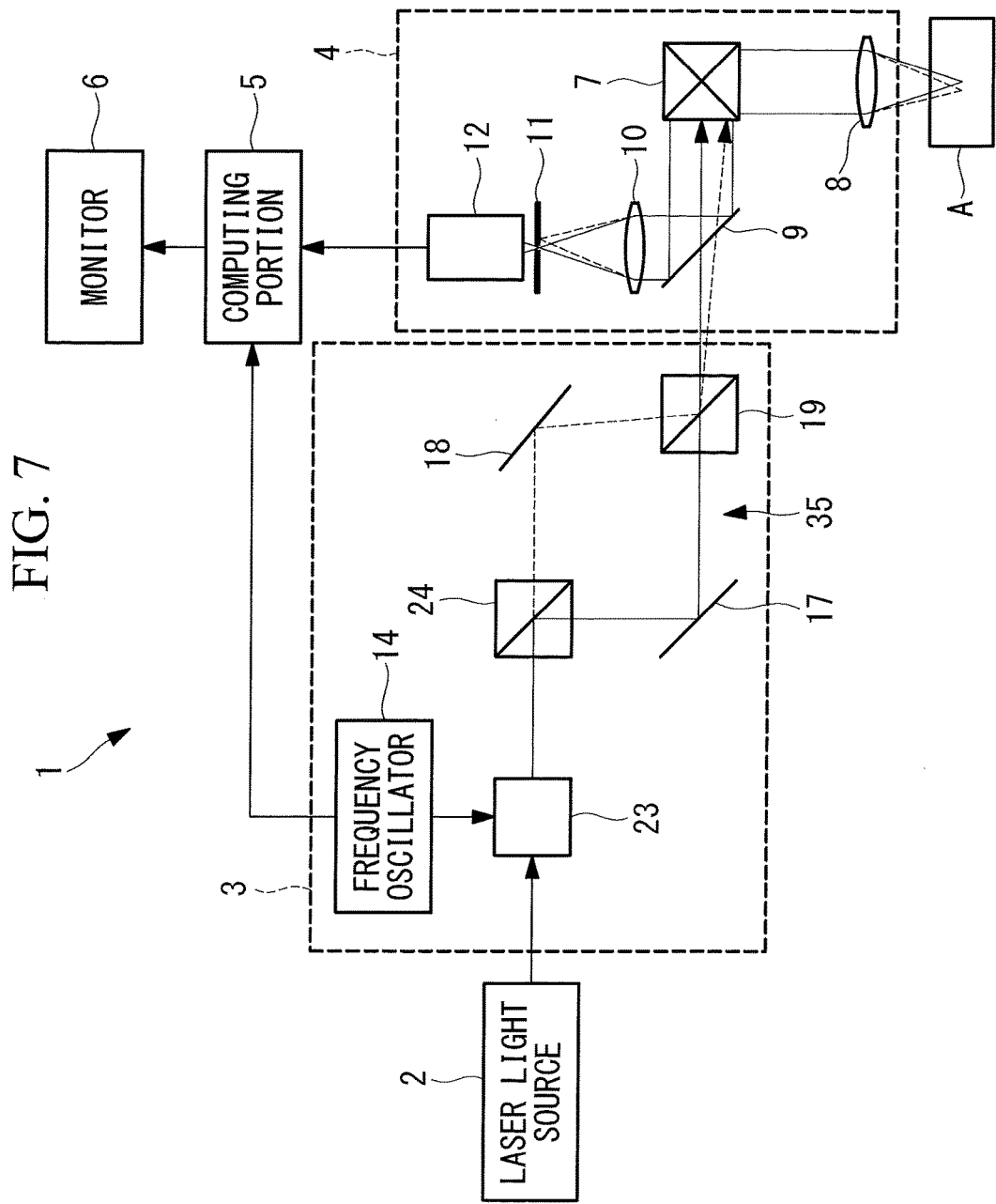
FIG. 7 is a diagram showing the overall configuration of a fourth modification of the microscope in FIG. 1.

In addition, as the laser light source 2 in this embodiment, as shown in FIG. 7, a unit provided with a laser light source 2 that continuously generates an excitation beam and an optical element 23 (for example, electro-optic element) that changes the polarization ratio of the excitation beam emitted from the laser light source 2 into an arbitrary repeating waveform may be employed instead of a unit that generates an excitation beam that oscillates at a predetermined cycle. In this case, the frequency at which the optical element 23 is driven and the frequency of the computing portion may be synchronized.

In this case, a polarizing beam splitter (demultiplexer) 24 is used as the first beam splitter.

By doing so, because it is not necessary to invert the flickering timings depending on the optical-path lengths, there is an advantage in that there is no need to ensure a large enough optical-path-length difference, and thus, it is possible to make the apparatus compact. In addition, with the optical element 23, it is possible to achieve higher-speed switching as compared with the case of using the movable mirror 13.

Figure 8:
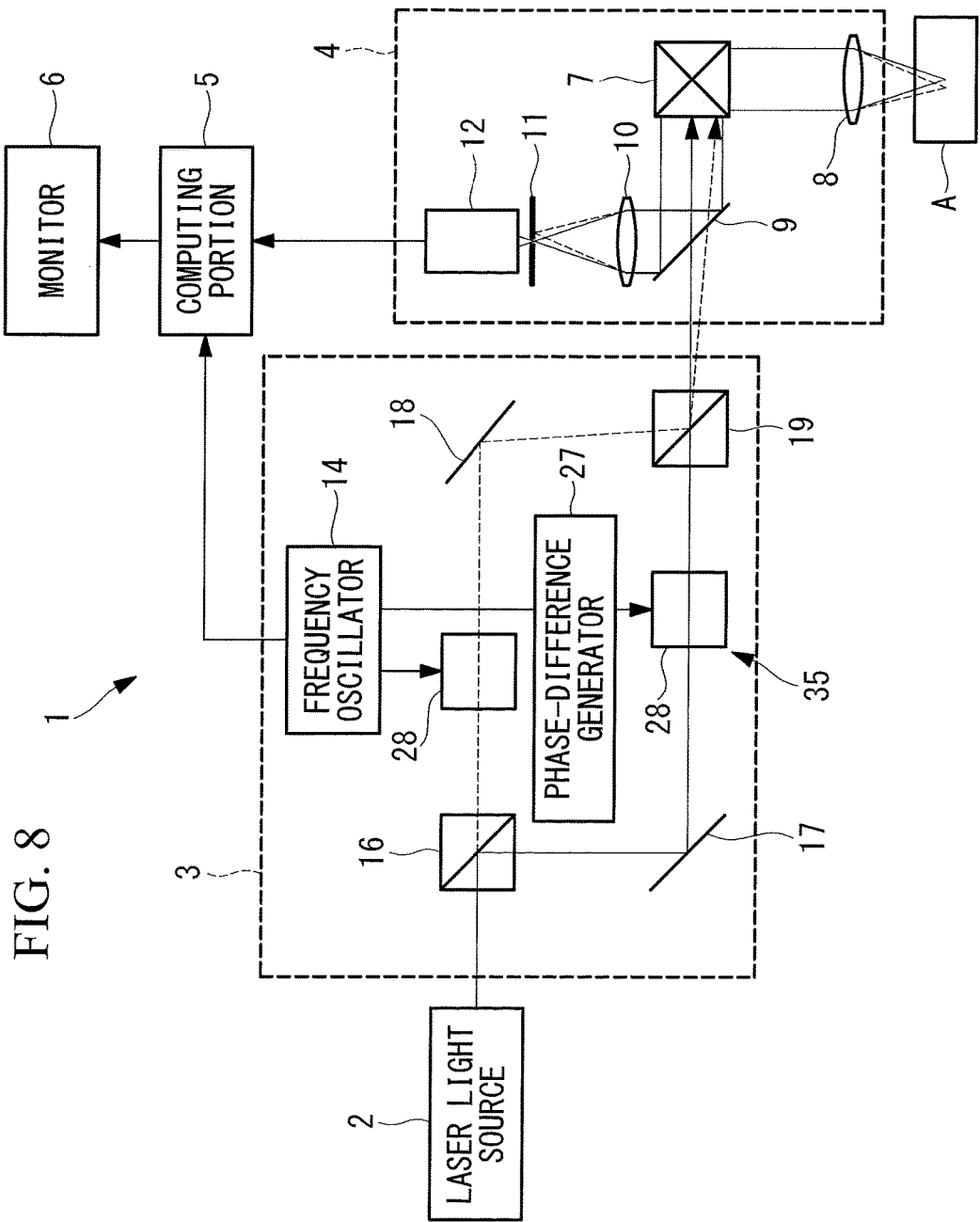
FIG. 8 is a diagram showing the overall configuration of a fifth modification of the microscope in FIG. 1.

In addition, in the case in which optical elements (for example, acousto-optic element) 28 that periodically change the excitation-beam intensities are used instead of the optical element 23, as shown in FIG. 8, the optical elements 28 are individually disposed in the two optical paths split by the demultiplexer 16, and the acousto-optic devices 28 are synchronized by using the frequency oscillator 14, thus modulating the excitation-beam intensities so as to invert the phases thereof. By doing so also, as with the case in which the optical element 23 is used, because it is not necessary to invert the flickering timings depending on the optical-path lengths, there is an advantage in that there is no need to ensure a large enough optical-path-length difference, and thus, it is possible to make the apparatus compact. In addition, it is possible to achieve higher-speed switching as compared with the case of using the movable mirror 13.

Figure 9:
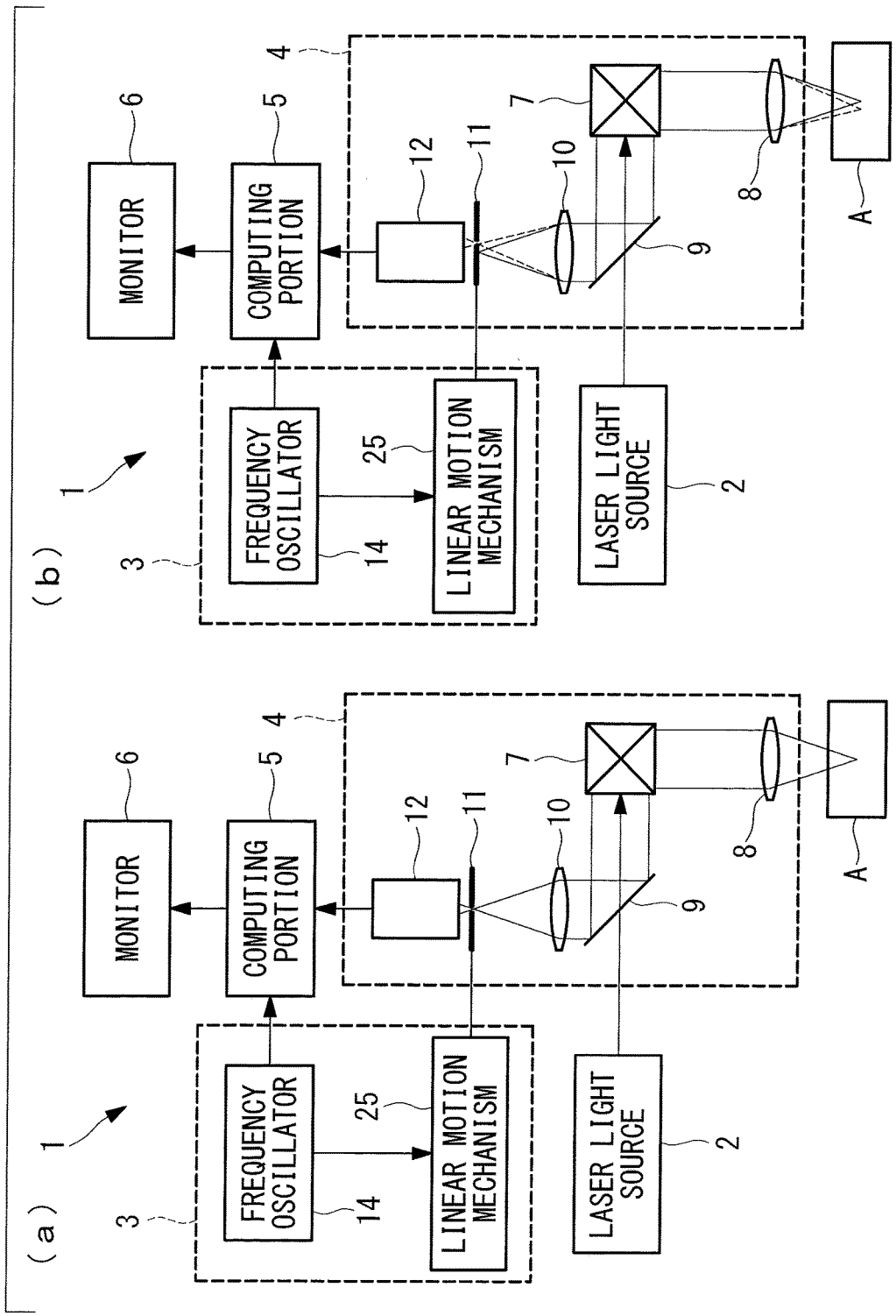
FIG. 9 is a diagram showing a sixth modification of the microscope in FIG. 1, which shows overall configurations (a) in which a pinhole is disposed at a conjugate position and (b) in which the pinhole is disposed at a non-conjugate position.

In addition, in the individual embodiments described above, although two excitation beams are prepared as the excitation beams to be made to enter the microscope main unit 4, alternatively, as shown in FIGS. 9(*a*) and (*b*), the positional relationships between the focal-point position of the objective lens 8 and the pinhole 11 may be switched between the conjugate positional relationship and the non-conjugate positional relationship by making one excitation beam enter and by moving the pinhole 11 in a direction that intersects the optical axis by using a linear motion mechanism 25.

In addition, in this embodiment, although differences between the fluorescences acquired by the light detector 12 are computed for individual pixels, the differences may be computed for individual images.

In addition, in the computing portion 5, although subtraction is performed by means of hardware by using the lock-in amplifier, alternatively, the computing portion 5 may be formed of a computer, and the differences may be computed by using software such as signal processing or the like.

Figure 10:
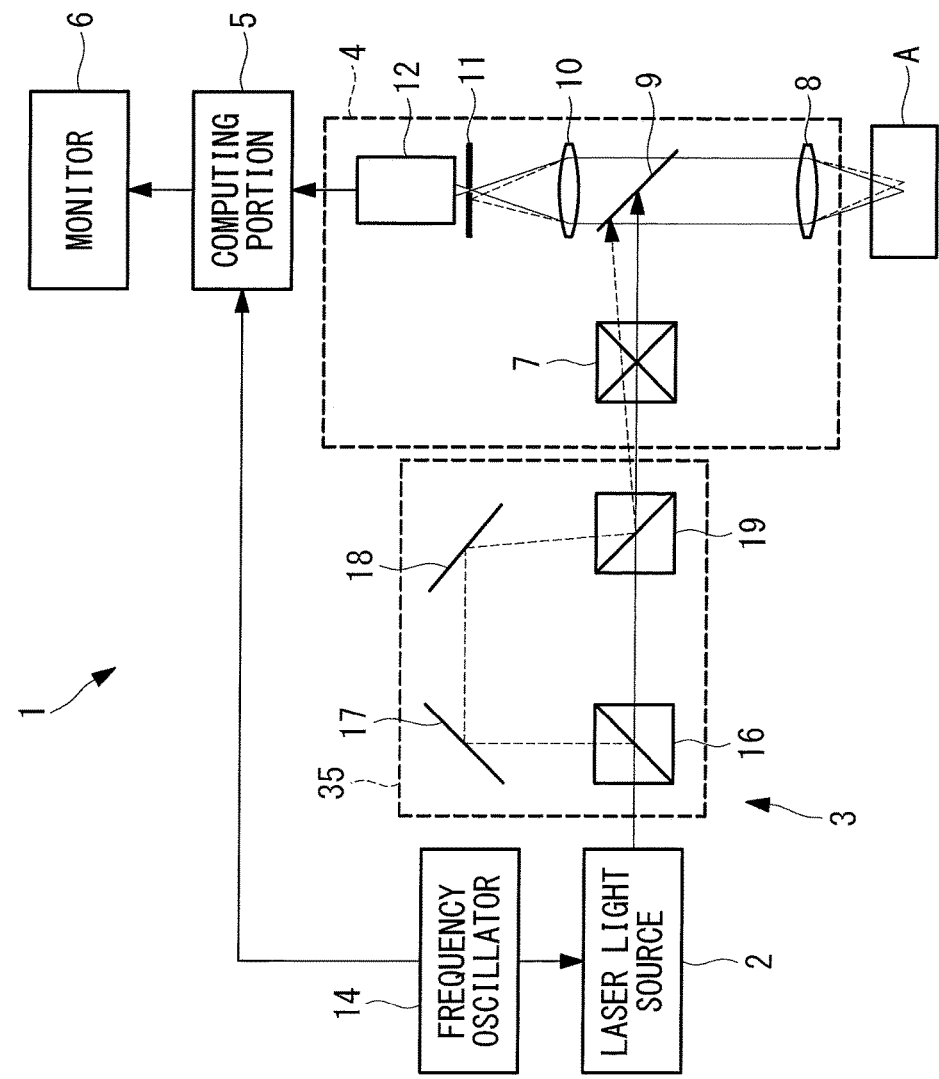
FIG. 10 is a diagram showing a seventh modification of the microscope in FIG. 1.

In addition, in this embodiment, although a confocal microscope that detects fluorescence collected by the objective lens 8 in the process of returning via the scanner 7 has been described as an example, alternatively, as shown in FIG. 10, a multiphoton excitation microscope may be employed. In this case, an ultrashort-pulse laser light source is used as the laser light source 2, and the excitation beams may be oscillated or switched at a frequency that is sufficiently greater than a pulse width on the order of femtoseconds. In addition, in the multiphoton excitation microscope also, the pinhole 11 may be disposed at a position that is in stage before the light detector 12 and that is optically conjugate with the focal-point position of the objective lens 8.

Figure 11:
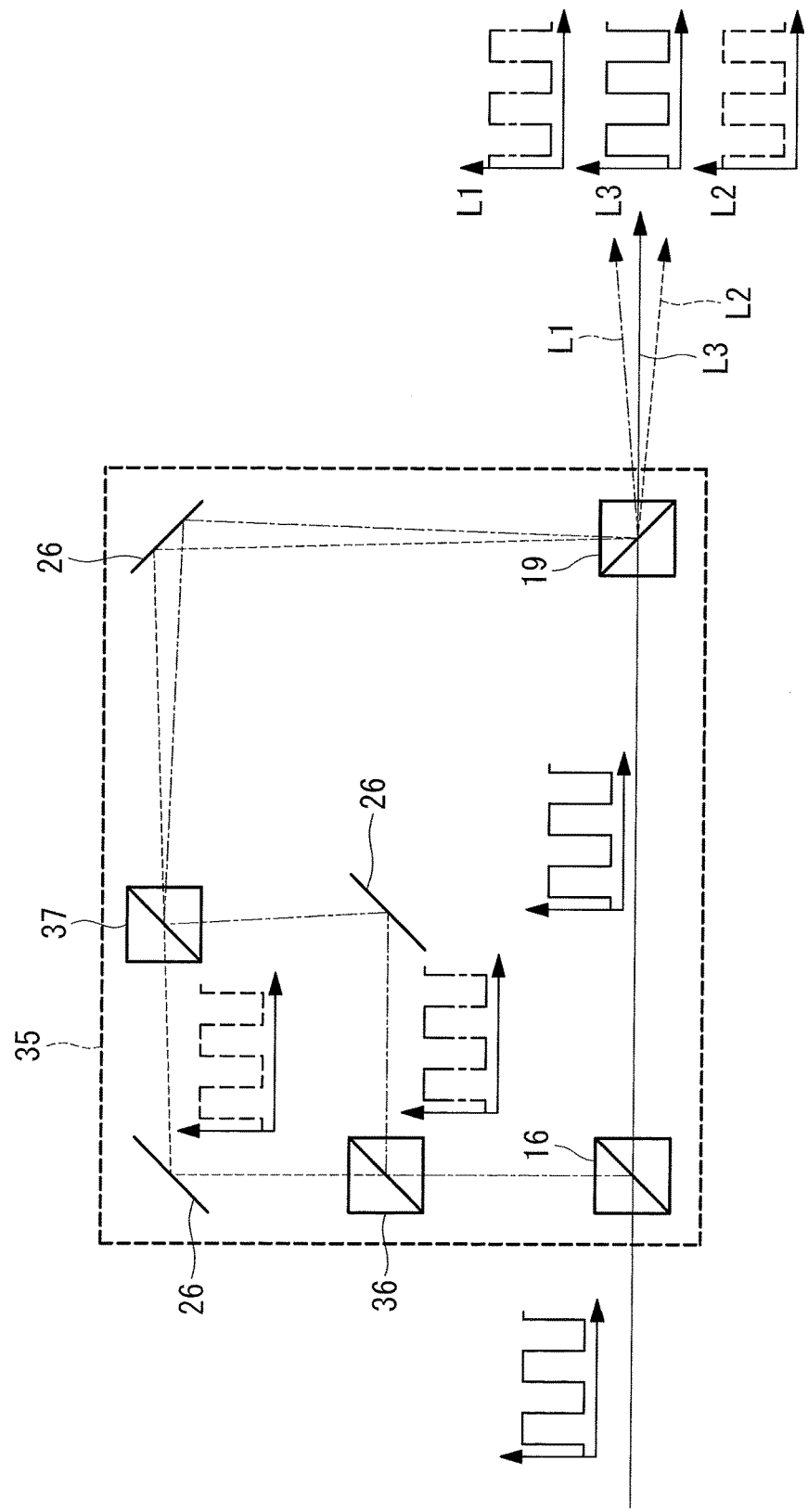
FIG. 11 is a diagram showing a modification of a spatial optical system of the microscope in FIG. 3.

In addition, in the individual embodiments described above, the differences are computed between two fluorescences, that is, the fluorescence generated by the excitation beam forming the focal point at a position that is optically conjugate with the pinhole 11 and the fluorescence generated by the excitation beam forming the focal point at a position that is optically non-conjugate with the pinhole 11, at the individual positions scanned by the scanner 7; however, there is no limitation thereto, the computation may be performed by detecting the fluorescences at multiple points. For example, as shown in FIG. 11, it is permissible to employ, as the spatial optical system 35 in FIG. 3, a system provided with a second demultiplexer 36 that further splits the second optical path split by the demultiplexer 16 and a second multiplexing portion 37 that multiplexes excitation beams that have passed along the two split optical paths.

By appropriately adjusting the angle of the mirror 26 that forms the optical path, it is possible to create two excitation beams that are made to enter the scanner 7 at different angles so that the light-focusing point in the specimen A and the pinhole 11 are set in a non-conjugate positional relationship. The phases of these two excitation beams L1 and L2 are the same and inverted with respect to that of an excitation beam L3 that has passed along the first optical path. In addition, the intensities of the two excitation beams L1 and L2 are half of that of the excitation beam L3. Therefore, at the computing portion, as in the following expression, a fluorescence F may be calculated by subtracting fluorescences acquired when the excitation beams L1 and L2 are radiated from a fluorescence F3 acquired when the excitation beam L3 is radiated:

$$F=F3-(F1+F2)$$

Figure 12:
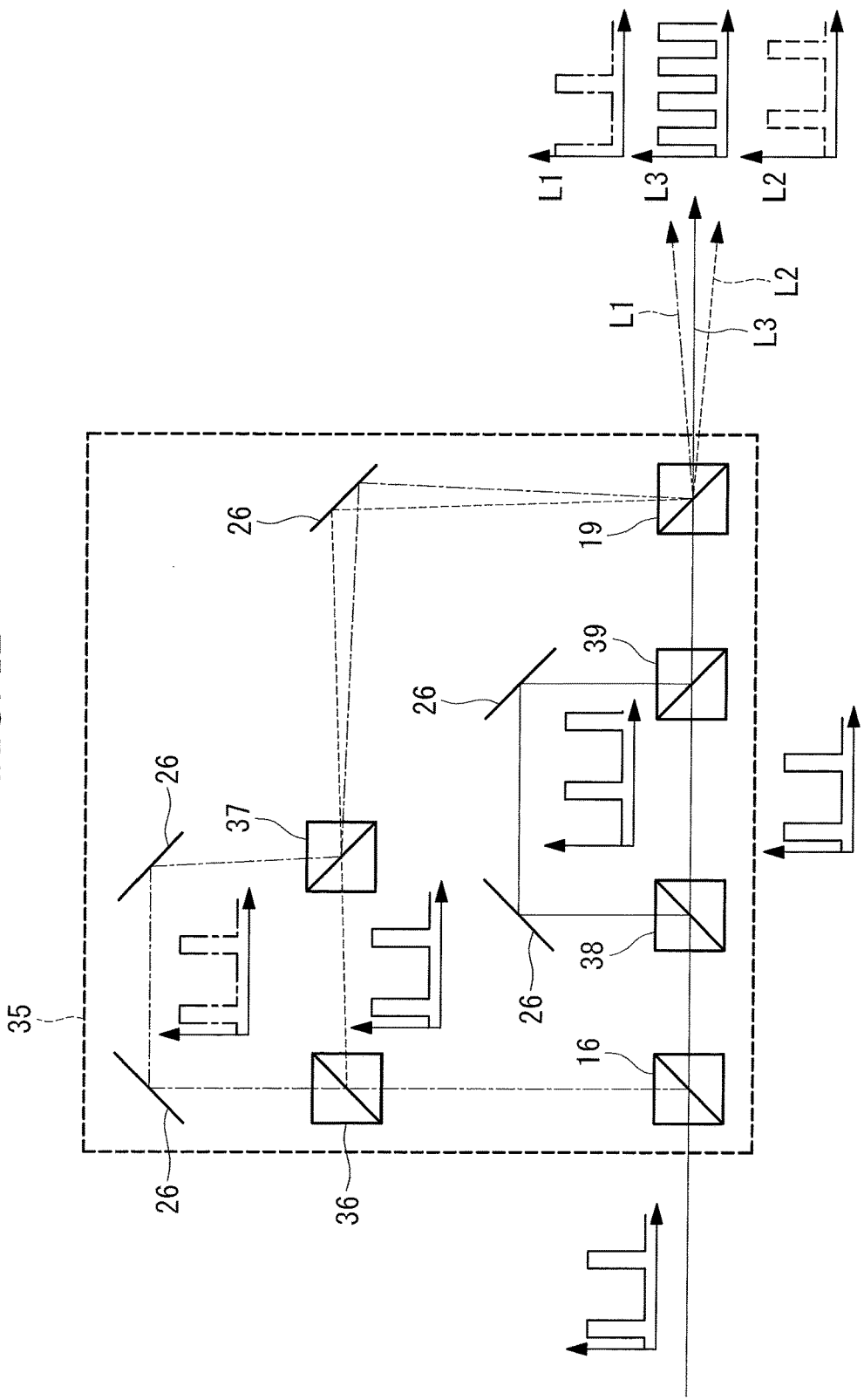
FIG. 12 is a diagram showing an additional modification of the spatial optical system in FIG. 11.

In addition, for example, as shown in FIG. 12, a demultiplexer 38 and a multiplexing portion 39 may be provided in the optical path of the excitation beam L3, in which the pinhole 11 and the light-focusing point of the excitation beam are set in a conjugate positional relationship, and the excitation beam L3 that oscillates at a frequency twice as great as that of the excitation beam that is made to enter from the laser light source 2 may be generated. In this case, the intensity of the excitation beam L3 becomes the same as those of the excitation beams L1 and L2. Therefore, at the computing portion, as in the following expression, the fluorescence F may be calculated by individually subtracting the fluorescences F1 and F2 acquired when the excitation beams L1 and L2 are radiated immediately after the excitation beam L3 from the fluorescence F3 acquired when the excitation beam L3 is radiated and by taking the average therebetween:

$$F=\{(F3-F1)+(F3-F2)\}/2$$

Note that, although the case where two excitation beams F1 and F2 are used has been described as an example, the excitation beam may be split into three or more.

Figure 13:
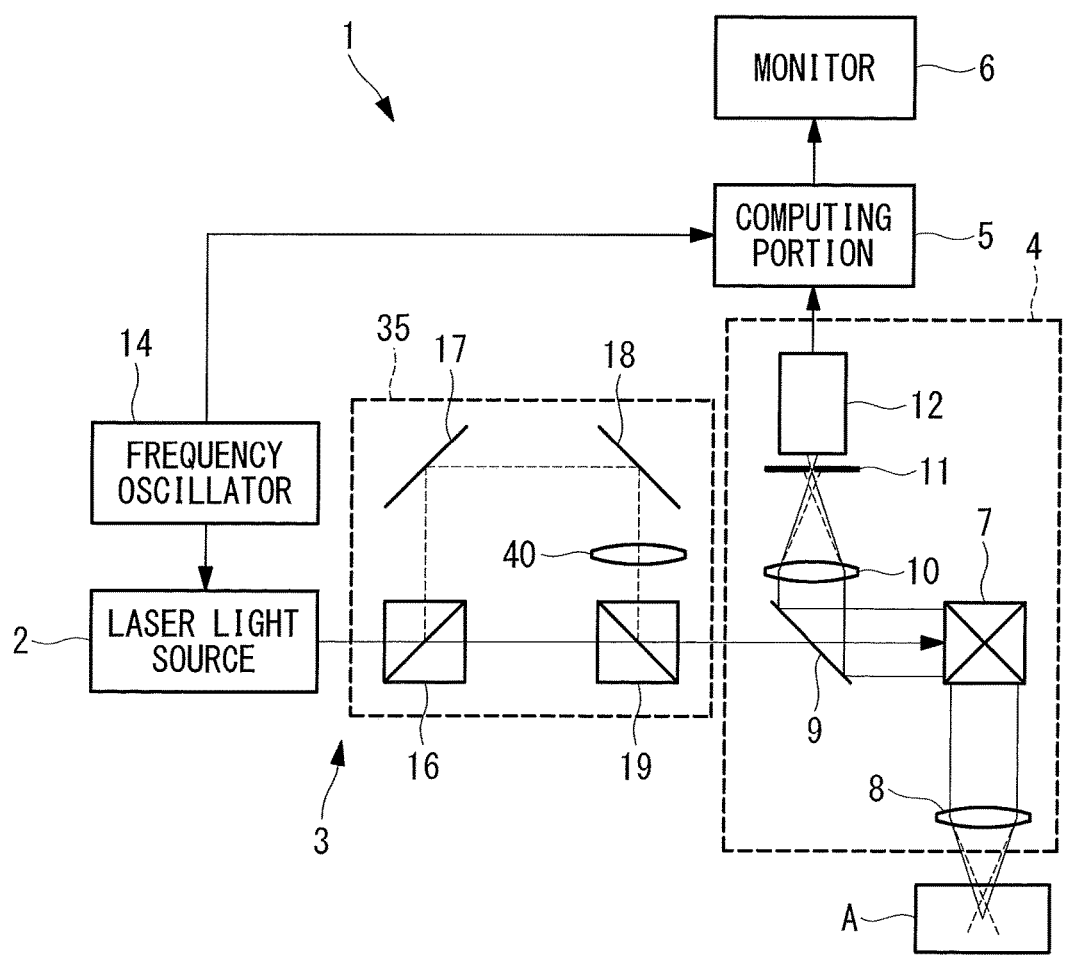
FIG. 13 is a diagram showing another modification of the spatial optical system of the microscope in FIG. 3.

In addition, in the individual embodiments described above, the positional relationship between the pinhole 11 and the light-focusing point of the excitation beam is switched to the optically non-conjugate positional relationship by making the excitation beam enter the scanner 7 at a different angle and by moving the light-focusing point of the excitation beam in a direction that intersects the optical axis; alternatively, however, as shown in FIG. 13, by disposing a lens 40 in the first optical path split by the demultiplexer 16, the non-conjugate positional relationship may be established by moving the light-focusing position of the excitation beam in the depth direction of the specimen A.

The above-described embodiment leads to the following inventions.

An aspect of the present invention provides a microscope including: a scanner that scans an excitation beam coming from a light source; an objective optical system that focuses the excitation beam scanned by the scanner onto a sample, and that, on the other hand, collects fluorescence generated at individual scanning positions in the sample; a detector that detects the fluorescence collected by the objective optical system; a light blocking member that is disposed between the detector and the objective optical system and that partially blocks the fluorescence collected by the objective optical system; a switching portion that switches, in a temporal manner, the positional relationship between the light blocking member and a light-focusing point of the excitation beam in the sample between an optically conjugate positional relationship, in which in-focus fluorescence generated at the light-focusing point passes through the light blocking member, and a non-conjugate positional relationship, in which the in-focus fluorescence does not pass through the same light blocking member as the light blocking member that has allowed the in-focus fluorescence to pass therethrough; and a computing portion that computes a difference between fluorescence signals acquired by the detector in the two positional relationships switched by the switching portion.

With this aspect, when the excitation beam coming from the light source is scanned by the scanner and is focused on the sample by the objective optical system, a fluorescent substance at the light-focusing point of the excitation beam in the sample is excited, thus generating fluorescence. The generated fluorescence is detected by the detector after being collected by the objective optical system, and a fluorescence image is generated by associating the intensity of the detected fluorescence with the scanning position.

In this case, when the positional relationship between the light blocking member provided in a stage before the detector and the light-focusing point of the excitation beam in the sample is switched to the conjugate positional relationship by operating the switching portion, in-focus fluorescence and off-focus fluorescence are detected by the detector. In addition, when the positional relationship between the light blocking member and the light-focusing point of the excitation beam in the sample is switched to the non-conjugate positional relationship by operating the switching portion, the in-focus fluorescence cannot pass through the light blocking member, and thus, only the off-focus fluorescence is detected by the detector. Then, by computing the differences between these fluorescence signals by using the computing portion, it is possible to obtain the in-focus fluorescence from which the off-focus fluorescence has been removed, and thus, it is possible to acquire a clear fluorescence image.

In the above-described aspect, the switching portion may relatively change the position of the light-focusing point of the excitation beam in the sample relative to that of the light blocking member.

By doing so, it is possible to set the relative position of the light-focusing point at a desired position by changing the light-focusing position or the position of the light blocking member.

In the above-described aspect, the switching portion may be provided with a deflection element that is disposed between the light source and the scanner and that changes an angle at which the excitation beam enters the scanner.

By doing so, by operating the deflection element, the excitation beam coming from the light source is made to enter the scanner at different timings by changing the incident angles thereof in accordance with the angle of the movable mirror. By doing so, it is possible to easily switch the positional relationship between the light blocking member and the light-focusing point of the excitation beam in the sample between the optically conjugate positional relationship and the non-conjugate positional relationship.

In addition, in the above-described aspect, the switching portion may move the light blocking member in a direction that intersects the optical axis.

By doing so, by moving the light blocking member to positions at which the fluorescence coming from the light-focusing point of the excitation beam is allowed to pass therethrough and positions at which the fluorescence coming from the light-focusing point of the excitation beam is not allowed to pass therethrough, it is possible to easily switch the positional relationship between the light blocking member and the light-focusing point of the excitation beam in the sample between the optically conjugate positional relationship and the non-conjugate positional relationship.

In addition, in the above-described aspect, the light source may make the excitation beam oscillate in an arbitrary repeating waveform, and the switching portion may be provided with a spatial optical system that splits the excitation beam into a plurality of optical paths and makes the split excitation beams enter the scanner at different angles and different phases.

By doing so, the excitation beam coming from the light source is split into two optical paths in the spatial optical system, and these are made to enter the scanner after the phases thereof are made different by passing along two optical paths having different optical-path lengths. Because the phases in which the excitation beams that have passed along the two optical paths enter the scanner are made different by the spatial optical system, it is possible to easily switch the positional relationship between the light blocking member and the light-focusing points of the excitation beams in the sample between the optically conjugate positional relationship and the non-conjugate positional relationship.

In addition, in the above-described aspect, the light source may continuously emit the excitation beam, and the switching portion may be provided with: an optical element that periodically switches polarization states of the excitation beam coming from the light source; a demultiplexer that splits the excitation beam output from the optical element into a plurality of optical paths in accordance with the polarization states thereof; and a spatial optical system that makes the excitation beams split by the demultiplexer enter the scanner at different angles and different phases.

By doing so, the excitation beam continuously emitted from the light source is made to enter the spatial optical system, with the polarization states thereof periodically being changed by the optical element, is split into the two optical paths by the demultiplexer depending on the polarization states thereof, and is made to enter the scanner at different angles and different phases. Accordingly, it is possible to easily switch the positional relationship between the light blocking member and the light-focusing points of the excitation beams in the sample between the optically conjugate positional relationship and the non-conjugate positional relationship.

In addition, in the above-described aspect, the light source may continuously emit the excitation beam, and the switching portion may be provided with: a demultiplexer that splits the excitation beam into a plurality of optical paths; optical elements that are provided in the individual optical paths split by the demultiplexer and that are synchronously driven to periodically change excitation-beam intensities; and a spatial optical system that makes the excitation beams enter the scanner at different angles and different phases.

By doing so, the excitation beam continuously emitted from the light source is made to enter the spatial optical system, is split into a plurality of optical paths by the demultiplexer, and is subsequently made to enter the scanner at different angles and different phases by synchronizing the optical elements provided in the individual optical paths. Accordingly, it is possible to easily switch the positional relationship between the light blocking member and the light-focusing point of the excitation beam in the sample between the optically conjugate positional relationship and the non-conjugate positional relationship.

In addition, in the above-described aspect, the light source may make the excitation beam oscillate in an arbitrary repeating waveform, and the switching portion may split the excitation beam into a plurality of optical fibers and set the length of the optical fibers and emitting angles so that the split excitation beams enter the scanner at different angles and different phases.

By doing so, the flickering excitation beam emitted from the light source is split into a plurality of optical fibers, is guided through the optical fibers set to have different lengths and emitting angles, and is subsequently made to enter the scanner at different angles and different phases. Accordingly, it is possible to easily switch the positional relationship between the light blocking member and the light-focusing points of the excitation beams in the sample between the optically conjugate positional relationship and the non-conjugate positional relationship.

In addition, in the above-described aspect, more than one of the light source may be provided, the plurality of the light sources may synchronously make the excitation beams oscillate in arbitrary repeating waveforms, and the switching portion may make the excitation beams coming from the individual light sources enter the scanner at different angles and different phases.

By doing so also, it is possible to easily switch the positional relationship between the light blocking member and the light-focusing points of the excitation beams in the sample between the optically conjugate positional relationship and the non-conjugate positional relationship.

In addition, in the above-described aspect, the computing portion may compute a difference between two images that are generated on the basis of fluorescence signals acquired by the detector in the two positional relationships switched by the switching portion.

In addition, in the above-described aspect, the computing portion may compute a difference between fluorescence signals acquired by the detector in the two positional relationships switched by the switching portion for individual pixels.

By doing so, because differences between fluorescence signals acquired at very small time intervals are computed for the individual pixels, it is possible to acquire a low-blur clear image even when a fast-moving subject is used.

In addition, another aspect of the present invention provides a microscopy method in which an excitation beam scanned by a scanner is focused on a sample by using an objective optical system, fluorescence generated at the individual scanning positions in the sample is collected by using the objective optical system, and the fluorescence that has passed through a light blocking member is detected by a detector, the microscopy method including: a first step of detecting the fluorescence by using the detector by setting a positional relationship between the light blocking member and a light-focusing point of the excitation beam in the sample in an optically conjugate positional relationship in which in-focus fluorescence generated at the light-focusing point passes through the light blocking member; a second step of detecting the fluorescence by using the detector by setting the positional relationship between the light blocking member and a light-focusing point of the excitation beam in the sample in an optically non-conjugate positional relationship in which the in-focus fluorescence does not pass through the same light blocking member as the light blocking member that has allowed the in-focus fluorescence to pass therethrough; and a third step of subtracting fluorescence signals detected by the detector in the second step from fluorescence signals detected by the detector in the first step.

REFERENCE SIGNS LIST

A specimen (sample)
1 microscope
2 laser light source (light source)
3 switching portion
5 computing portion
7 scanner
8 objective lens (objective optical system)
11 pinhole (light blocking member)
12 light detector (detector)
3 movable mirror (deflection element)
15 spatial optical system (switching portion)
16 demultiplexer
20 optical fiber
20b fiber beam splitter (switching portion)
20c, 20d second optical fiber (optical fiber)
21, 22 laser light source (light source)
23 optical element
24 polarizing beam splitter (demultiplexer)
25 linear motion mechanism (switching portion)

The invention claimed is:

1. A microscope comprising:
a scanner configured to scan an excitation beam coming from a light source;
an objective optical system configured to focus the excitation beam scanned by the scanner onto a sample, and to collect fluorescence generated at individual scanning positions in the sample;
a detector configured to detect the fluorescence collected by the objective optical system;
a light blocking member disposed between the detector and the objective optical system configured to partially block the fluorescence collected by the objective optical system;
a switch disposed between the light source and the scanner, the switch being configured to change, in a temporal manner, a position of the light-focusing point of the excitation beam in the sample relative to that of the light blocking member between a first relative position, in which in-focus fluorescence generated at the light-focusing point passes through the light blocking member, and a second relative position, in which the in-focus fluorescence does not pass through the light blocking member; and
a controller configured to compute a difference between fluorescence signals acquired by the detector in the first and second relative positions.

2. A microscope according to claim 1, wherein the switch is provided with a deflection element that changes an angle at which the excitation beam enters the scanner.

3. A microscope according to claim 1, wherein the switch moves the light blocking member in a direction that intersects an optical axis of the objective optical system.

4. A microscope according to claim 1,
wherein the light source makes the excitation beam oscillate in an arbitrary repeating waveform, and
the switch is provided with a spatial optical system that splits the excitation beam into a plurality of optical paths and makes the split excitation beams enter the scanner at different angles and at different phases.

5. A microscope according to claim 1,
wherein the light source continuously emits the excitation beam, and
the switch is provided with: an optical element that periodically switches polarization states of the excitation beam coming from the light source; a demultiplexer that splits the excitation beam output from the optical element into a plurality of optical paths in accordance with the polarization states thereof; and a spatial optical system that makes the excitation beams split by the demultiplexer enter the scanner at different angles and at different phases.

6. A microscope according to claim 1,
wherein the light source continuously emits the excitation beam, and
the switch is provided with: a demultiplexer that splits the excitation beam into a plurality of optical paths; optical elements that are provided in the individual optical paths split by the demultiplexer and that are synchronously driven to periodically change excitation-beam intensities; and a spatial optical system that makes the excitation beams enter the scanner at different angles and at different phases.

7. A microscope according to claim 1,
wherein the light source makes the excitation beam oscillate in an arbitrary repeating waveform, and
the switch splits the excitation beam into a plurality of optical fibers and sets a length of the optical fibers and emitting angles so that split excitation beams enter the scanner at different angles and at different phases.

8. A microscope according to claim 1,
wherein a plurality of light sources are provided, the plurality of the light sources synchronously make excitation beams oscillate in arbitrary repeating waveforms, and
the switch makes the excitation beams coming from the individual light sources enter the scanner at different angles and at different phases.

9. A microscope according to claim 1, wherein the controller computes the difference between two images that are generated on the basis of the fluorescence signals acquired by the detector in the first and second relative positions.

10. A microscope according to claim 1, wherein the controller computes the difference between the fluorescence signals acquired by the detector in the first and second relative positions for individual pixels of the detector.

11. A microscopy method in which an excitation beam scanned by a scanner is focused on a sample by using an objective optical system, fluorescence generated at the individual scanning positions in the sample is collected by using the objective optical system, and the fluorescence that has passed through a light blocking member is detected by a detector, the microscopy method comprising:
switching, in a temporal manner, a position of the light-focusing point of the excitation beam in the sample relative to that of the light blocking member between a first relative position, in which in-focus fluorescence generated at the light-focusing point passes through the light blocking member, and a second relative position, in which the in-focus fluorescence does not pass through the light blocking member;
detecting the fluorescence with the detector at the first relative position;
detecting the fluorescence with the detector at the second relative position; and
subtracting fluorescence signals detected by the detector in the second relative position from fluorescence signals detected by the detector in the first relative position.

* * * * *